United States Patent [19]

Gusella et al.

[11] Patent Number: 4,594,318

[45] Date of Patent: Jun. 10, 1986

[54] ISOLATION AND LOCALIZATION OF DNA SEGMENTS

[75] Inventors: James F. Gusella, Framingham; David Housman, Watertown; Cheryl Keys, Worcester, all of Mass.; Aviva Varsanyi-Breiner, Ness-Ziona, Israel; Theodore T. Puck, Denver, Colo.; Carol Jones, Denver, Colo.; Fa-Ten Kao, Denver, Colo.

[73] Assignee: Massachusetts Institute of Technology, Cambridge, Mass.

[21] Appl. No.: 403,771

[22] PCT Filed: Apr. 29, 1981

[86] PCT No.: PCT/US81/00576

§ 371 Date: May 17, 1982

§ 102(e) Date: May 17, 1982

[51] Int. Cl.$^4$ .................... C12Q 1/68; C12N 15/00; C12P 19/34

[52] U.S. Cl. .................... 435/6; 435/172.3; 435/91; 935/6; 935/78; 935/80

[58] Field of Search ............ 435/5, 6, 172, 91, 172.3; 935/6

[56] References Cited

PUBLICATIONS

Lewin, Benjamin, "Gene Expression", Eucaryotic Chromosomes, John Wiley & Sons, v. 2, 1980, pp. 244–252.

Wu, Ray, "Recombinant DNA", Methods in Enzymology, Academic Press, v. 68, 1979, pp. 389–395.

Hardman, Joel G., et al, "Hormone Action", Methods in Enzymology, Academic Press, v. XXXIX, 1975, pp. 122–128.

Gusella, James, et al, "Precise Localization of Human B-globin Gene Complex on Chromosome 11*", (DNA hybridization/hemoglobin B Chain/Hemoglobin o Chain/Regional Gene Mapping), Proc. Nat'l. Acad. Sci. USA, V. 76, No. 10, Oct. 1979, pp. 5239–5243.

Maniatis, Tom, et al, "The Isolation of Structural Genes from Libraries of Eucaryotic DNA", Cell, V. 15, Oct. 1978, pp. 687–701.

Varsanyi-Breiner, A., et al, "The Organization of a Nuclear DNA Sequence from a Higher Plant: Molecular Cloning and Characterization of Soybean Ribosomal DNA", Elsevier/North-Holland Biomedical Press, Amsterdam, Gene 7, (1979), pp. 317–334.

Blattner, F., et al., Reports, "Cloning Human Fetal γ Globin and Mouse α-Type Globin DNA: Preparation and Screening of Shotgun Collections, Science, v. 202, AAAS, 1978, pp. 1279–1284.

Benton, W. David, et al., "Screening λ gt Recombinant Clones by Hybridization to Single Plaques in Situ", Science, v. 196, Apr. 8, 1977, pp. 180–182.

Rigby, Peter W., et al., "Labeling Deoxyribonucleic Acid to High Specific Activity in Vitro by Nick Translation with DNA Polymerase I", J. Mol. Biol., v. 113, 1977, pp. 237–251.

Kao, Fa-Ten, et al., "Genetics of Somatic Mammalian Cells: Genetic, Immunologic, and Biochemical Analysis with Chinese Hamster Cell Hybrids Containing Selected Human Chromosomes*", Proc. Nat. Acad. Sci., USA, Genetics, v. 73, No. 1, Jan. 1976, pp. 193–197.

Kao, Fa-Ten, et al, "Genetics of Cell-Surface Antigens: Regional Mapping of Three Components of the Human Cell-Surface Antigen Complex, $A_L$, On Chromosome 11[1]", Somatic Cell Genetics, v. 3, No. 4, 1977, pp. 421–429.

(List continued on next page.)

Primary Examiner—Alvin E. Tanenholtz
Attorney, Agent, or Firm—Kenway & Jenney

[57] ABSTRACT

A process of isolating and identifying cloned DNA segments from defined regions of a chromosome by preparing a series of cell hybrids from a first species and a second species, which hybrids contain a chromosome or deletion mutant of a chromosome as the only chromosomal component of the second species, constructing a library of recombinant clones of DNA from the hybrid cell, plaquing the library on culture plates, transferring the plaques onto a medium which is capable of holding DNA in a covalent or noncovalent fashion, hybridizing the medium to total (nick-translated) radioactive second species DNA, and collecting the radioactive 2d species plaques.

1 Claim, 2 Drawing Figures

| | CYTOGENETIC REGION | MARKER | RECOMBINANT DNA PROBE |
|---|---|---|---|
| | pfer→p13 | SAII-1,-3 | HII-II |
| | p13→p1208 | LDHA | HII-8, HII-13 |
| | p1208→pII | Hbβ,δ,γ,ACP2 | HβGI |
| | pII→q13 | CENTROMERE | HII-3, HII-6 |
| | q13→qter | SAII-2 | |

PUBLICATIONS

Davidson, Eric H., et al, "Regulation of Gene Expression: Possible Role of Repetitive Sequences", AAAS, Science, v. 204, Jun. 8, 1979, pp. 1052–1059.

Blattner, Frederick R., et al., "Charon Phages: Safer Derivatives of Bacteriophage Lambda for DNA Cloning", Laboratory of Genetics, Madison, WI, Apr. 8, 1977, pp. 161–169.

Britten, R. J., et al., "Repeated Sequences in DNA", Science, v. 161, No. 3841, Aug. 9, 1968, pp. 529–540.

Southern, E. M., "Detection of Specific Sequences Among DNA Fragments Separated by Gel Electrophoresis", J. Mol. Biol. (1975) v. 98, pp. 503–517.

McConaughy, Betty L., et al, "Related Base Sequences in the DNA of Simple and Complex Organisms, VI. The Extent of Base Sequences Divergence Among the DNAs of Various Rodents", Biochemical Genetics, n. 4, 1970, pp. 425–446.

Thuring, R. W. J., et al., "A Freeze-Squeeze Method for Recovering Long DNA from Agarose Gels", Analytical Biochemistry, v. 66, 1975, pp. 213–220.

ISOLATION AND LOCALIZATION OF DNA SEGMENTS

The Government has rights in this invention pursuant to Contract Number CA-5-14051 awarded by the Department of Health and Human Services, Contract Number PCM 77-17747 awarded by the National Science Foundation, and Contract Number 1-713 awarded by the National Foundation-March of Dimes.

The present invention relates to a novel process for isolating and identifying cloned DNA segments from defined regions of a chromosome.

BACKGROUND OF THE INVENTION

As stated in applicants' article entitled "Isolation and Localization of DNA Segments from Specific Human Chromosomes", *Proc. Nat'l. Acad. SCI. USA*, Vol. 77, No. 5, pp. 2829–2833, May 1980, there are two principal reasons for attempting to achieve as complete as possible fine-structure analysis of the human genome. First, delineation of the DNA sequence of individual genes and construction of the corresponding probes now can be used to detect the presence of human genetic disease. These procedures can be applied in utero so that birth of tragically defective babies can be prevented. Second, and perhaps of even greater importance to biomedical science, definition of DNA sequences over large chromosomal regions, including sequences specifying protein structure as well as the noncoding intervals within and between these sequences, appears to promise greater understanding of physiological and biochemical mechanisms of human gene regulation. The genetic data so obtained should illuminate many aspects of medicine and developmental biology including situations not usually considered to lie within the narrow scope of the term "genetic disease."

Mammalian gene mapping has made significant progress in recent years, particularly by means of cytogenetic identification of relatively gross regions on each chromosome and by development of powerful methods for determining DNA sequences. However, one of these techniques operates at the level of millions of base pairs whereas the other is limited to handling of thousands. Therefore, a large gap in revolving power exists which must be bridged before these techniques can be combined for high-resolution mapping of the human genome. The present invention demonstrates how this gap can be filled.

The recombinant DNA methods used previously isolated and characterized cloned DNA segments based on their ability to code for a specific mRNA. With the novel process described herein, cloned DNA segments can be isolated and characterized based on their genetic map position alone.

DESCRIPTION OF THE PREFERRED EMBODIMENTS

Figures 1, 2:
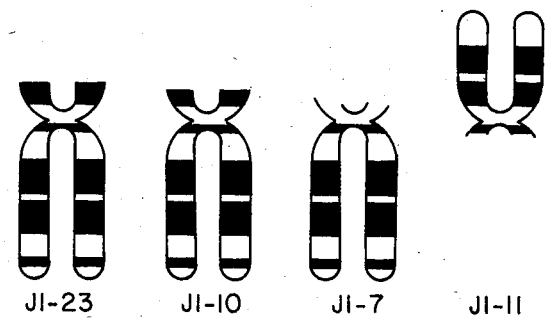
FIG. 1 is a diagram showing the various terminal deletions of human chromosome 11 in four cell hybrids.
FIG. 2 is a schematic representation of human chromosome 11 with arrows indicating the breakpoints at which terminal deletions occurred in the four clones.

The object of the instant invention is to isolate DNA segments of a size permitting complete sequence analysis from a chromosome and to map these segments precisely on the chromosome.

This object has been achieved by:

(1) Preparing a series of cell hybrids from a first species and a second species, said cell hybrids containing a chromosome or deletion mutant of a chromosome as the only chromosomal component of the second species.

(2) Partially digesting the hybrid cell DNA with a restriction enzyme and then size fractionating the partially digesting DNA on a sucrose gradient in order to isolate DNA fragments 15–20 kb in length.

(3) Ligating the DNA fragments to a bacteriophage.

(4) Using an in vitro encapsidation procedure to obtain viable phage containing the ligated DNA.

(5) Propogating the phages to obtain a library of recombinant clones of DNA from the hybrid cell.

(6) Plaquing the library on culture plates.

(7) Transferring the plaques onto a medium which is capable of holding DNA in a covalent or non-covalent fashion.

(8) Hybridizing the medium of (7) to total, nicktranslated radioactive 2d species DNA.

(9) Collecting the radioactive 2d species plaques.

(10) Digesting the DNA from each corresponding phage clone with a restriction enzyme in order to produce subfragments.

(11) Fractionating the subfragments on an agarose gel.

(12) Staining the subfragments with ethidium bromide in order to visualize the DNA fragments.

(13) Transferring the subfragments onto a medium which is capable of holding DNA in a covalent or non-covalent fashion.

(14) Hybridizing the medium of (13) to total nick-translated radioactive 2d species DNA.

(15) Creating a radioactive single copy DNA probe by nick-translating to high specific activity the fragments that did not hybridize to the probe.

(16) Hybridizing the radioactive single copy DNA probe with DNAs from a battery of mutant hybrid cell clones containing successively larger terminal deletions of the 2d species chromosome in order to localize the DNA fragment on the chromosome.

With regard to (1), any two different species can be used. This is because the repetitive DNA sequences of each species, which are interspersed throughout the genome many thousand times, have been found to be species-specific. Thus, in (8) and (14), hybridization of a repetitive DNA probe to DNA from clones of a library constructed from genomic DNA of a hybrid cell will distinguish the species origin of the cloned DNA segments.

With regard to (2) and (10), any restriction enzyme can be used. Restriction enzymes useful in the invention include, but are not limited to EcoRI, Bam II, SacI, Hind III, Xba I and Hae III.

With regard to (3) any bacteriophage may be used. An example of a bacteriophage useful in the invention is λCharon 4A.

With regard to (6) any type of culture plate may be used, but a petri plate is preferably used.

With regard to (7) and (13) any medium which is capable of holding DNA in a covalent or noncovalent fashion can be used, but nitrocellulose filter paper is the medium preferably used.

The invention is further illustrated by the following non-limiting example.

EXAMPLE 1

All manipulation involving viable recombinant phage were performed at the P2-ER2 level of containment in accordance with the National Institutes of Health Guidelines for Recombinant DNA Research.

DNA was prepared from the human HeLa and the Chinese hamster ovary (CHO-K1) cell lines and from a human—CHO-K1 hybrid, J1-11, which contained a deletion mutant of chromosome II as the only human chromosomal component. The procedure utilized in making human Chinese hamster cell hybrids was that set forth in Puck, T. et al., Proc. Nat. Acad. Sci., USA; Vol. 68 pp. 3102-3106 (1971), the teachings of which are incorporated herein by reference. The procedure utilized in preparing the DNA from these hybrid cells was that set forth in Precise localization of human B-globin gene complex on Chromosome 11, James Gusella et al., Proc. Natl. Acad. Sci. USA, Vol. 76, No. 10, pp 5239-5243, October 1979, the teachings of which are incorporated by reference. The J1-11 hybrid cell DNA was partially digested with Eco-R1 and was then size fractionated on a sucrose gradient in order to isolate DNA fragments 15-20 kb in length. The procedure utilized in digesting the DNA with ECO-R1 was that set forth in Precise localization of human B-globin gene complex on Chromosome 11, James Gusella et al., Proc. Natl. Acad. Sci. USA, Vol. 76, No. 10, pp. 5239-5243, October 1979, the teachings of which are incorporated by reference.

λCharon 4A bacteriophage arms were separated from the internal fragments by sucrose gradient centrifugation of Eco-R1 digested phage DNA. The procedure utilized in separating the λCharon 4A arms from the internal fragments was that set forth in The Isolation of Structural Genes from Libraries of Evcaryotic DNA, Mariatis, T. et al., Cell, Vol. 15, pp. 687-701, October 78, the teachings of which are incorporated by reference. The isolated DNA fragments from the hybrid cell were then ligated to the λCharon 4A arms and an in vitro encapsidation procedure was used to obtain viable phage containing the ligated DNA. The procedure utilized in ligating the DNA fragments to the λCharon 4A arms was that set forth in The Organization of a Nuclear DNA Sequence from a Higher Plant: Molecular Cloning and Characterization of Soybean Ribosomal DNA, Aviva Varsanyi—Breiner et al., Gene, 7, (1979) pp. 317-334 the teachings of which are incorporated by reference. The procedure utilized in performing the in vitro encapsidation procedure was that set forth in Cloning Human Fetal γ Globin and Mouse α-Type Globin DNA: Preparation and Screening of Shotgun Collections, Blattner et al., Science, Vol. 202, pp. 1279-1284, December 1978, the teachings of which are incorporated by reference. These phage were propogated to obtain a J1-11 library of recombinant clones and the library was then plaqued on Petri plates. The procedure utilized in obtaining the library was that set forth in The Organization of a Nuclear DNA Sequence from a Higher Plant: Molecular Cloning and Characterization of Soybean Ribosomal DNA, Aviva Varsanyi—Breiner et al., Gene, 7 (1979) pp. 317-334 the teachings of which are incorporated by reference. Grids of recombinant phages were obtained by transfer, with sterile toothpicks, of individual plagues, from plates with 100-300 plague-forming units onto a fresh lawn on a 150 mm bacterial dish.

Duplicate nitrocellulose filters were prepared from each grid and hybridized to total nick-translated HeLa cell DNA or CHO-K1 DNA respectively ($10^6$ cpm/filter; specific activity, $2 \times 10^8$ cpm/µg). The procedure utilized in preparing the nitrocellulose filters from each grid was that set forth in Screening λgt Recombinant Clones by Hybridization to Single Plaques in situ, Benton, W. & Davis, R. Science, Vol. 196, pp. 180-182, 1977, the teachings of which are incorporated by reference. The procedure utilized in the nick translation of the DNA was that set forth in Labeling Deoxyribonucleic Acid to High Specific Activity in Vitro by Nick Translation with DNA Polymerase 1, Rigby et al., S. Mol. Biol., Vol. 113, pp. 237-251 (1977), the teachings of which are incorporated by reference. Clones containing human DNA were then chosen by virtue of their hybridization to HeLA DNA but not to CHO-K1 DNA.

A systematic survey of more than 20,000 clones from the J1- 11 library yielded approximately 50 recombinants of putative human origin. 5 clones were selected at random from these 50 clones for further characterization.

The DNA from one of the 5 clones, H11-3 was digested with Eco-R1 and Bam H1 and fractionated on a 1% agarose gel. The DNA fragments were then visualized by staining with ethidium bromide. Eco-R1 digestion of clone H11-3 DNA produced four fragments: the λCharon 4A arms, (X and Z), a dimer of the λCharon 4A aims (c, d, e and h) and five contained at least some of the human cloned sequence (a, b, f, g, and i).

After visualization of the DNA fragments, the DNA was transferred to a nitrocellulose filter and hybridized to high specific-activity, 32p human DNA ($2 \times 10^8$ cpm/µg). Although fragment Y from the Eco-RI digestion and fragments b and f from the Bam H1digestion hybridized to the human DNA probe and therefore, contained some reiterated human DNA sequences, three fragments (a, g and i) produced by Bam H1 digestion did not hybridize to the probe under these conditions and therefore were presumed to contain only single-copy DNA. One of these fragments, g, was chosen as a probe for further hybridization experiments.

To localize this cloned DNA segment (g) to a specific region of chromosome 11, DNA was isolated from CHO-K1, J1, which carries the entire human chromosome 11 on a Chinese hamster background and the four cell lines J1-11, J1-23, J1-10 and J1-7 which contain specific deletions in chromosome 11.

FIG. 1 is a diagram showing the various terminal deletions of human chromosome 11 in four cell hybrids; and FIG. 2 is a schematic representation of human chromosome 11 with arrows indicating the break-points at which terminal deletions occurred in the four clones. Based on the pattern of restriction fragments shown by clone H11-3, we expected to observe hybridization to EcoRI digested DNA of cell lines that carried this 15-kb DNA fragment. As expected, hybridization was observed in this region on the gel in DNA samples from clones J1 and J1-11. The pattern of hybridization to clones J1-7, J1-10 and J1-23 was used to ascertain the chromosomal location of the DNA fragment isolated and cloned in H11-3. The presence of intense hybridization in DNA isolated from all three lines indicated that the H11-3 DNA segment was located in the centromere-linked region delineated by the breakpoints of clones J1-11 and J1-7 (FIG. 1).

A similar set of experiments was performed for each of the other 4 clones chosen for analysis. In each case, a single copy DNA was selected for mapping of the corresponding 15 to 20 kb fragment on chromosome 11. The map positions of these DNA sequences are listed in Table 1.

TABLE 1

Localization of cloned DNA sequences on human chromosome 11.

| DNA clone | Cell line | | | | | | Locus |
|---|---|---|---|---|---|---|---|
| | CH0-K1 | J1 | J1-11 | J1-23 | J1-10 | J1-7 | |
| H11-3 | − | + | + | + | + | + | p11 → q13 |
| H11-6 | − | + | + | + | + | + | p11 → q13 |
| HβG1 | − | + | + | + | + | − | p13 → p1208 |
| H11-13 | − | + | + | + | − | − | p13 → p1208 |
| H11-11 | − | + | + | − | − | − | pter → p13 |

We claim:

1. A process for the isolation of human repetitive DNA fragments comprising:
   (a) isolating 15 to 20 kilobase human DNA fragments;
   (b) inserting the human DNA fragments of step a into the DNA of lambda bacteriophage to form a clone;
   (c) screening the ligated phage DNA for clones containing human DNA;
   (d) isolating the DNA from the clones of step c containing human DNA;
   (e) fragmenting the isolated DNA of step d;
   (f) resolving the fragments of step e;
   (g) hybridizing the resolved fragments of step f with human DNA using molecular hybridizing conditions which only identify fragments with human repetitive DNA sequences, wherein said repetitive DNA fragments are isolated from and are unique to human chromosomes.

* * * * *